(12) United States Patent
Kim et al.

(10) Patent No.: US 7,972,608 B2
(45) Date of Patent: Jul. 5, 2011

(54) CARRIER PROTEINS FOR VACCINES

(75) Inventors: John Kim, Raleigh, NC (US); Francis J. Michon, Bethesda, MD (US)

(73) Assignees: Baxter International Inc., Deerfield, IL (US); Baxter Healthcare S.A. (CH)

( * ) Notice: Subject to any disclaimer, the term of this patent is extended or adjusted under 35 U.S.C. 154(b) by 941 days.

(21) Appl. No.: 10/562,256

(22) PCT Filed: Jun. 23, 2004

(86) PCT No.: PCT/US2004/020026
§ 371 (c)(1),
(2), (4) Date: Jun. 28, 2006

(87) PCT Pub. No.: WO2005/000346
PCT Pub. Date: Jan. 6, 2005

(65) Prior Publication Data
US 2007/0014812 A1    Jan. 18, 2007

(51) Int. Cl.
*A61K 39/08* (2006.01)
(52) U.S. Cl. .................................................. 424/239.1
(58) Field of Classification Search .................. None
See application file for complete search history.

(56) References Cited

U.S. PATENT DOCUMENTS

| | | | |
|---|---|---|---|
| 5,443,966 A | | 8/1995 | Fairweather et al. |
| 5,785,973 A | * | 7/1998 | Bixler et al. ............ 424/196.11 |
| 5,993,825 A | * | 11/1999 | Jennings et al. ........... 424/244.1 |
| 6,602,508 B2 | * | 8/2003 | Michon et al. ............ 424/244.1 |

FOREIGN PATENT DOCUMENTS

| | | |
|---|---|---|
| EP | 0 427 347 A1 | 5/1991 |
| WO | WO 95/04151 A2 | 2/1995 |
| WO | WO 99/15671 A1 | 4/1999 |
| WO | WO 2004011027 A1 * | 2/2004 |

OTHER PUBLICATIONS

Wessels et al. (Infection and Immunity, vol. 66, no. 5, pp. 2186-2192, May 1998).*
Wessels et al. (Journal of Clinical Investigation, vol. 86, pp. 1428-1433 Nov. 1990).*
Michon et al. (in Streptococci and Host. (Ed). Horaud et al. Plenum Press, New York, pp. 847-850, 1997).*
Database Biosis Online, XP-002302424, Oct. 14, 2003; Kim et al., "Tetanus Toxin C-Fragment as a Universal Carrier Protein for Conjugate Vaccines" *Abstracts of the Interscience Conference on Antimicrobial Agents and Chemotherapy,* vol. 43, p. 294, Sep. 14-17, 2003.
International Search Report for PCT/US2004/020026, dated Nov. 15, 2004.

* cited by examiner

*Primary Examiner* — Gary B. Nickol
*Assistant Examiner* — Khatol Shahnan-Shah
(74) *Attorney, Agent, or Firm* — Kenneth H. Sonnenfeld; King & Spalding LLP

(57) ABSTRACT

The present invention provides, among other things, improved carrier proteins for antigen-based vaccines, including polysaccharide-based vaccines. An aspect of the invention advantageously employs tetanus toxin Fragment C.

6 Claims, 6 Drawing Sheets

FIGURE 1

Schematic Representation of Tetanus Toxin

NH₂ — 2 — 457 S—S 458 — 864-865 (←Papain) — 1315 — COOH

← Light chain → ← Heavy chain →

← B-fragment → ← C-fragment →

FIGURE 2

**Elution Profile and MW of Tetanus Toxin C-Fragment:
Native vs. Recombinant**

Superose 6 Profiles

- - - TTc (Native)
—— rTTc (Recombinant)

Absorbance ($UV_{280}$)

Minutes: 10, 20, 30, 40, 50

| Tetanus Toxin C-Fragment | Ave MW (MALDI-TOF MS) |
|---|---|
| TTc (Native) | 51,732.1 |
| rTTc (Recombinant) | 51,788.7 |

CARRIER PROTEINS FOR VACCINES

The present invention relates to improved carrier proteins for antigen-based vaccines, including polysaccharide-based vaccines.

BACKGROUND OF THE INVENTION

Conjugation of a polysaccharide to a carrier protein can effectively make that polysaceharide more immunogenic. Tetanus toxoid has been used for decades in this capacity as a carrier, and its safety profile has been established, at least in the context of past uses.

The structural gene for tetanus toxin has been cloned and sequenced. Fairweather et al., J. Bacteriol. 165: 21-27 (1986); Fairweather et al., Nuci. Acid Res. 14: 7809-7812 (1986). These studies have confirmed the structure of tetanus toxin as a 150 kD protein comprising 1315 amino acids. Fragment C, which constitutes the binding portion of native tetanus toxin, is a 52 kD polypeptide generated by papain cleavage of the toxin and corresponds to the 451 amino acids at the C-terminus. See FIG. 1.

Tetanus toxoid has been found to contain 2 to 3 universal T-cell epitopes. Demotz et al., J. Immunol 142: 394-402 (1989). This feature makes tetanus toxoid highly effective in humans. Fragment C of the toxoid has been shown to be nontoxic. This fragment also contains at least one of the universal immunogenic T cell epitopes recognized by primed donors. Valmori et al., J. Immunol 149:717-2 1 (1992); Panina-Bordignon et al., Eur. J. Immunol. 19: 2237 (1989).

Capsular polysaccharides (CP) conjugate vaccines targeting a variety of bacterial infections are currently under development and clinical evaluation. The inclusion of multiple CP serotypes combined in a single injection is currently under study. The combination of CP conjugate vaccines into a single multivalent injection, however, can result in competition among the different components and adversely affect the immunogenicity of any individual conjugate. Fattom et al., Vaccine 17:126-33 (1999).

Tetanus toxoid is finding increased use in polysaccharide vaccines. There is now concern arising that the vaccinated population will be over exposed to Tetanus, with the risk of inducing tolerance and/or hypersensitivity throughout the population. For example, injection of mice with an immunogenic dose of carrier followed by immunization with hapten-carrier conjugate selectively suppresses antihapten antibody response. This carrier-induced epitopic suppression may be related to the induction of carrier-specifics T cells which in turn could inhibit selectively antihapten response. Epitopic suppression may induced through the expansion of the clones specific for the carrier epitopes and antigenic competition between hapten and carrier epitopes. Schutze et al., J. Immunol. 37: 2635-40 (1989). In humans, it has been demonstrated that prior immunity against a carrier protein modulates the serological response to synthetic conjugate vaccines. Di John et al., Lancet 2 (8677):1415-8 (1989). Barrington et al. (Infect. & Immun. 61: 432-8, 1993) have shown that epitopic suppression of antibody response to *Haemophilus influenzae* type b conjugate vaccine by preimmunization with vaccine components was observed. More recently, Burrage et al. (Infect. & Immun. 70: 4946-54, 2002) have shown some epitopic suppression of antibody response to meningococcal C conjugate vaccine by preimmunization with the tetanus carrier protein. In mice, epitopic suppression to the antibody response of pneumococcal and meningococcal polysaceharide-tetanus conjugates was observed after high doses of carrier priming with tetanus toxoid (Peeters et al. Infect & Immun 59: 3504-10, 1991). Due to these potential adverse consequences, tetanus toxoid should no longer be administered as it has in the past, and therefore improved carriers are needed.

SUMMARY OF THE INVENTION

In order to avoid many of the adverse consequences associated with current practices, the present invention provides carriers based upon Fragment C of the tetanus toxoid.

In accordance with an aspect of the invention, methods for the production of immunogenic conjugate vaccines utilizing Fragment C of tetanus toxoid are provided.

In accordance with another aspect of the invention, a conjugate antigen comprising one or more polysaccharide moieties from at least one target pathogen covalently linked to a tetanus toxoid Fragment C protein moiety is provided. As used herein, "target pathogen" may refer to any exogenous pathogen comprising a polysaceharide epitope which may be recognized by the immune system of a mammal or avian, such as a bacterial or fungal pathogen.

In accordance with yet another aspect of the invention, a vaccine comprising a conjugate antigen comprising one or more polysaceharide moieties from at least one target pathogen covalently linked to a tetanus toxoid Fragment C protein moiety is provided.

In accordance with yet another aspect of the invention, a method for eliciting an immune response to a target pathogen in a mammal or avian comprising the step of inoculating the mammal or avian with an effective amount of a vaccine comprising a conjugate antigen comprising one or more polysaceharide moieties from at least one target pathogen covalently linked to a tetanus toxoid Fragment C protein moiety is provided. The method may be practiced on avians such as chickens, turkeys, emus, ostriches, and other commercially important birds. The method is preferably practiced on mammals such as rodents, equines, bovines, other commercially important herd mammals, canines, felines, other companion animals, and humans. Particularly, the method may be practiced on humans.

In accordance with yet another aspect of the invention, a method for preventing a subsequent infection of a mammal or avian by a target pathogen comprising the step of inoculating the mammal or avian with an effective amount of a vaccine comprising a conjugate antigen comprising one or more polysaceharide moieties from at least one target pathogen covalently linked to a tetanus toxoid Fragment C protein moiety is provided. The method may be practiced on avians such as chickens, turkeys, emus, ostriches, and other commercially important birds. The method is preferably practiced on mammals such as rodents, equines, bovines, other commercially important herd mammals, canines, felines, other companion animals, and humans. Particularly, the method may be practiced on humans.

BRIEF DESCRIPTION OF THE FIGURES

FIG. 1 is a schematic depiction of the Tetanus toxin.

FIG. 2 depicts the profile and molecular weight of the native and recombinant TTc.

DETAILED DESCRIPTION

Figure 3:
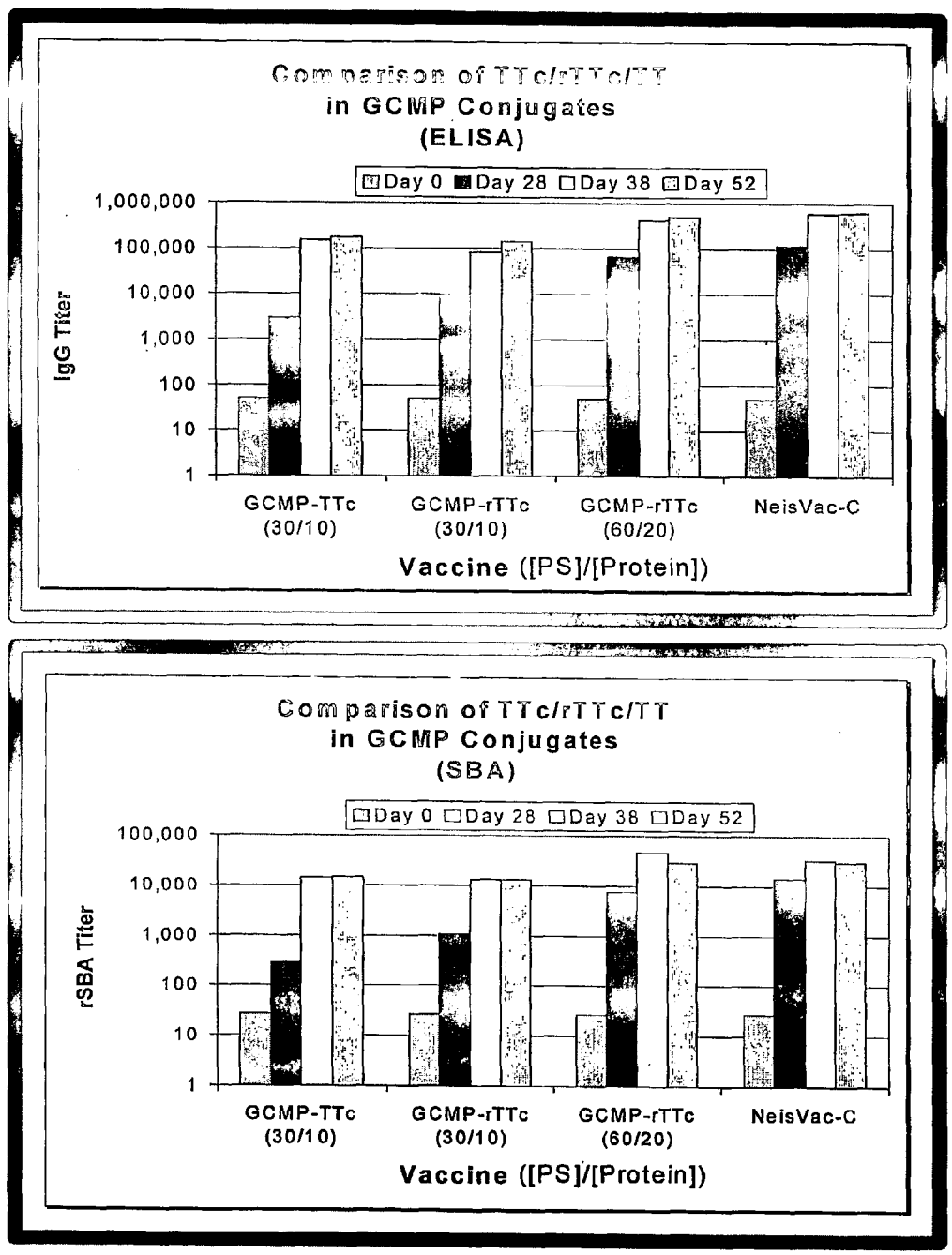
FIG. 3 depicts comparisons of Fragment C, recombinant Fragment C and the Tetanus Toxoid with Group C Meningococcal Polysaccharide (GCMP) conjugates.

As disclosed for the first time herein, Fragment C of tetanus toxin, often referred to as "TTc", can be used as a carrier protein for polysaccharides, such as for capsular polysaccharide vaccines for protection against bacterial or fungal infections. Fragment C when conjugated to an antigen can increase the immunogenicity of that antigen, meaning that the ability of that antigen to elicit an immune response is enhanced through conjugation to Fragment C. This enhancement often has been referred to as the carrier effect, which in essence transforms the polysaccharide from a T-independent to a T-dependent antigen. The apparent lack of neutralizing Tetanus toxin antibodies in the animals immunized with polysaccharide TTc conjugates and the resulting reduction in recognition of the native tetanus toxoid, together with the apparent conservation of carrier ability, makes TTc an attractive substitute for Tetanus toxoid.

The data presented herein demonstrate that TTc and a recombinant TTc (rTTc) can be used as carrier for polysaccharides and elicit an immune response equivalent to that of Tetanus toxoid in terms of polysaccharide-specific IgG antibodies. See FIG. 2. These antibodies have a high functional activity as measured by the ability to kill the bacteria.

Fragment C (TTc) relates to the carboxyl-terminal portion of about amino acid positions 865-1315, as depicted in FIG. 1. Thus, in the context of the present invention, Fragment C refers to separation of the region from at least a portion of the remainder of the whole tetanus toxoid molecule, which can be done by digestion of the toxoid with papain or other proteases or through recombinant expression of the fragment. Recombinant expression of Fragment C is disclosed in U.S. Pat. No. 5,443,966. Accordingly, and vaccine comprising an antigen conjugated to Fragment C will lack at least a portion of the non-Fragment C (that is, the B fragment in FIG. 1) region.

Of course, various additions, deletions and substitutions can be made to the TTc sequence to yield variants without adversely impacting the carrier capabilities of the molecule. For example, conservative and semi conservative amino acid substitutions can be undertaken. Exemplary conservative amino acid substitutions include, but are not limited to, changes of: alanine to seine; arginine to lysine; asparigine to glutamine or histidine; aspartate to glutamate; cysteine to seine; glutamine to asparigine; glutamate to aspartate; glycine to proline; histidine to asparigine or glutamine; isoleucine to leucine or valine; leucine to valine or isoleucine; lysine to arginine, glutamine, or glutamate; methionine to leucine or isoleucine; phenylalanine to tyrosine, leucine or methionine; seine to threonine; threonine to serine; tryptophan to tyrosine; tyrosine to tryptophan or phenylalanine; valine to isoleucine or leucine. As will be appreciated by those of ordinary skill in the protein engineering arts, the conservative and semi conservative mutations mentioned herein are preferably made to regions outside of the recognized antigenic/immunogenic region of TTc. Suitable regions for mutation for various purposes (e.g., the addition of a polypeptide "tag" for ease of purification of the protein) include the C-terminal and N-terminal regions.

Variants can be created by recombinant techniques employing genomic or cDNA cloning methods. Site-specific and region-directed mutagenesis techniques can be employed. See CURRENT PROTOCOLS IN MOLECULAR BIOLOGY vol. 1, ch. 8 (Ausubel et al. eds., J. Wiley & Sons 1989 & Supp. 1990-93); PROTEIN ENGINEERING (Oxender & Fox eds., A. Liss, Inc. 1987). In addition, linker-scanning and PCR-mediated techniques can be employed for mutagenesis. See PCR TECHNOLOGY (Erlich ed., Stockton Press 1989); CURRENT PROTOCOLS IN MOLECULAR BIOLOGY, vols. 1 & 2, supra. Protein sequencing, structure and modeling approaches for use with any of the above techniques are disclosed in PROTEIN ENGINEERING, loc. cit. and CURRENT PROTOCOLS IN MOLECULAR BIOLOGY, vols. 1 & 2, supra. If desired, other variations to Fragment C can be undertaken by employing combinatorial chemistry, biopanning and/or phage display.

Peptide mimetics of Fragment C can be produced by the approach outlined in Saragovi et al., *Science* 253: 792-95 (1991) and other articles. Mimetics are peptide-containing molecules which mimic elements of protein secondary structure. See, for example, Johnson et al., "Peptide Turn Mimetics" in BIOTECHNOLOGY AND PHARMACY, Pezzuto et al., Eds., (Chapman and Hall, New York, 1993). The underlying rationale behind the use of peptide mimetics is that the peptide backbone of proteins exists chiefly to orient amino acid side chains in such a way as to facilitate molecular interactions, such as those of antibody and antigen. A peptide mimetic carrier according to the present invention would when administered to a host assist in eliciting an immune response.

Fragment C can be conjugated to the polysaccharide, such as a bacterial or fungal capsular polysaccharide, by methodologies currently in practice. For example, polysaccharides can by deacylated with treatment under slightly basic conditions, and then conjugated to Fragment C via reductive amination with a reducing agent, such a cyanoborohydride anions. See EP 0 658 118 B 1. Other conjugation approaches are available to the skilled person, such as those in the examples which follow and those disclosed in W00010599A2, U.S. Published Patent Application No. US 2001/0014332 A1. Another conjugation approach is described by Marburg et al., (J. Am. Chem. Soc., 108, 5282 1986) using bigenic spacers and is also disclosed in U.S. Pat. No. 4,695,624; U.S. Pat. No. 4,830,852; U.S. Pat. No. 4,882, 317 and U.S. Pat. No. 5,623,057 which is an improved process over the last three.

Sources of polysaccharide, which will define the type and specificity of vaccine, can be obtained from a wide variety of sources, including bacteria and fungi. Exemplary bacteria include: *Neisseria meningitidis*, including groups A, B, C, Y, W135 and X; *Streptococcus*, including groups A, B, and C; *Pneumococcus*, including types 1, 2, 3, 4, 6A, 6B, 9, 14, 18F, 19F and 23; *Staphylococcus aureus* including types 5 and 8; *Haemophilus influenzae*, including type b; *Mycobacterium tuberculosis; Campylobacter* spp.; enteroinvasive *Escherichia coli* isolates; *Salmonella typhii; Vibrio cholerae; Shigella flexneri; Brucella* spp.; *Francicella tularensis*; and *Yersinia pestis*. Particularly, antigens from *Neisseria meningitidis, Haernophilius influenzae, Pneumococcus*, and *Streptococcus* may be utilized for conjugation to TTc. Exemplary fungi include among others *Candida albicans, Cryptococcus neoformans*, and *Aspergillus niger*. Using standard carbohydrate chemistries, synthetic. polysaccharides having one or more characteristics of natural CPs can be employed as vaccines.

Fragment C, including variants, can be used as a carrier in much the same way as the present tetanus toxoid is. Pharmaceutically acceptable formulations for the conjugates include aqueous solutions, non-toxic excipients, including salts, preservatives, buffers and the like, as described in UNITED STATES PHARMACOPEIA AND NATIONAL FORMULARY (USP 24-NF 19); REMINGTON'S PHARMACEUTICAL SCIENCES; HANDBOOK ON PHARMACEUTICAL EXCIPIENTS (2d ed., Wade and Weller eds., 1994). Examples of non-aqueous solvents are propylene glycol, polyethylene glycol, vegetable oil and injectable organic esters such as ethyloleate. Aqueous solvents include water, alcoholic/aqueous solutions, saline solutions, parenteral vehicles such as sodium chloride, Ringer's dextrose, etc. Intravenous vehicles include fluid and nutrient replenishers. Preservatives include antimicrobials, anti-oxidants, chelating agents and inert gases. The pH and exact concentration of the various components of the binding composition are adjusted according to routine skills in the art. See GOODMAN AND GILMAN'S THE PHARMACOLOGICAL BASIS FOR THERAPEUTICS (9th ed.). In addition, one or more adjuvants may be added to the vaccine composition. Alum (aluminum hydroxide) is an example of a generally accepted adjuvant for use, although other adjuvants are know to those of skill in the vaccine arts.

Fragment C as part of a polysaccharide conjugate vaccine will usually be administered by a single dose (toddlers and adults) or multiple discrete doses for primary immunization (infant regimen) and as booster shots over a period of time. The specific dose level, and thus the therapeutically-effective amount, for any particular patient can depend on age, weight and sex. Although, as is true with most vaccines, normalized values can be established to develop generalized dosages that are effective across a population of group or sub-populations. Generally, vaccines containing from about 5 to about 100 μg, preferably about 10 to 50 μg, are suitable to elicit effective levels of antibody in young mammals against capsular polysaccharides of pathogenic gram negative or gram positive organisms, and can be further defined via titration and the like. Several small doses given sequentially would be expected to be superior to the same amount of conjugate given as a single injection.

The invention is further described by the following examples, which are illustrative of the invention but do not limit the invention in any manner.

Example 1

Preparation of rTTc Conjugates

Preparation of Group C Meningococcal Polysaccharides (GCMP), Group Y Meningococcal Polysaccharides (GYMP) and Group W Meningococcal Polysaccharides (GWMP):

The meningococcal C, Y and W polysaccharides were purified from fermentation broths, containing glucose and yeast extract.

De-O-acetylated (dOA) GCMP was prepared as disclosed in U.S. Pat. No. 5,425,946.

De-O-acetylated GYMP was prepared as follows:

Polysaccharide capture by ultrafiltration (UF) with a 300 kDa molecular weight cut off (MWCO) membrane:

Approximately 13 L of cell-free microfiltered fermentation permeate is concentrated by UF to approximately 1 liter using a Biomax 300K PELLICON® membrane (0.5 m$^2$). The concentrated retentate is diafiltered 12× against 1M NaCl and then 10× against DI water. It is further concentrated to approximately 0.2 L and collected.

Base Hydrolysis of the Polysaccharide:

The 300K retentate solution (ca 5 mg PS/mL) was adjusted to a final concentration of 2N NaOH. and placed in an oven set to 80° C. for 16-18 hrs. After the reaction mixture had cooled off to less than 50° C., it was diluted into 10 L of DI water. After concentration through a 30 kDa MWCO PELLICON® membrane, the concentrated retentate was diafiltered 12 times against 1 M NaCl and then 10 times against DI water. It was further concentrated to approximately 0.2 L and collected.

Acid Hydrolysis of the dOA GYMP:

The retentate solution was transferred to a teflon reaction and sodium acetetate (NaOAc) was added to a final concentration of 0.1 N. The reaction mixture was adjusted to pH5 using 6N HCl and placed in a water bath set to 7° C. It was shaken at 65 rpm until the polysaccharide reached a target MW of approximately 10-20 kDa as measured by Size Exclusion Chromatography Multi-Angle Laser Light Scatter (SEC-MALLS) using a Superose 12 (Pharmacia) column.

Re-N-Acetylation of the Fragmented doA Polysaccharide:

The pH of the solution was adjusted to 8 with 6N HCl solution, and acetic anhydride was then added dropwise at room temperature to a final concentration of 0.8 M acetic anhydride. 5N NaOH was used to keep the reaction mixture pH between 7 and 9. After completion of the reaction, the pH of the reaction mixture was increased to 13, and the mixture stirred an additional 1.5 hr. The reaction pH was then adjusted to pH 8 with 6N HCl solution. The reaction mixture was poured into 4 L of 1 M NaCl, concentrated to approximately 1 L using a Biomax 100K PELLICON® membrane (0.5 m$^2$) and the permeate collected. The 100K final permeate is concentrated by UF to approximately 1 liter using a Biomax 5K PELLICON® membrane (0.5 m$^2$). The concentrated retentate is diafiltered 10 times against DI water, then concentrated to approximately 0.2 L and collected. The fragmented polysaccharide was then activated with sodium metaperiodate to generate aldehyde groups in its sialic acid residues.

The oxidized polysaccharides were then conjugated by reductive amination using sodium cyanoborohydride to tetanus toxoid (Serum Statens Institute, Copenhagen, Denmark) or a recombinant form (*E. coli*) of tetanus toxin C fragment (rTTc) (Roche Molecular Biochemicals, Indianapolis, Ind.). Biochemical comparison of the recombinant form of tetanus toxin C fragment from Roche and C fragment isolated from tetanus toxin (TTc) after papain digestion (List Biological Laboratories, Inc. Campbell, Calif.) indicated that both proteins were identical (same AA composition, same MW as measured by MALDI-TOFF, and same elution profile by HPLC). See FIG. 2.

Some of the physicochemical characteristics of these conjugates are shown in Table 1 below.

TABLE 1

| Conjugate | [PS] (μg/mL) | [Protein] (μg/mL) | [PS]/ [Protein] | Yield PS % | Yield Protein % |
|---|---|---|---|---|---|
| GCMP-rTTc | 347.1 | 441.0 | 0.787 | 27.8 | 88.2 |
| GCMP-TT | 294.2 | 621.2 | 0.474 | 11.3 | 71.4 |
| GYMP-RTTc | 166.4 | 379.0 | 0.439 | 13.3 | 75.8 |
| GYMP-TT | 167 | 656.3 | 0.254 | 25 | 98 |
| GWMP-RTTc | 261.1 | 391.2 | 0.667 | 20.9 | 78.2 |
| GWMP-TT | 69.5 | 200.9 | 0.346 | 8.3 | 60 |

Three of the most clinically important Group B streptococcal (GB S) serotypes (Ia, III and V) polysaccharides were coupled by reductive amination to both tetanus toxoid and rTTc. See U.S. Pat. No. 5,993,825. Table 2 sets forth some of their characteristics.

TABLE 2

| Conjugate | [PS] (µg/mL) | [Protein] (µg/mL) | [PS]/ [Protein] | Yield PS % | Yield Protein |
|---|---|---|---|---|---|
| GBS Ia-RTTc | 307 | 279 | 1.1 | 25 | 59 |
| GBS Ia-TT | 200 | 240 | 0.8 | 23 | 60 |
| GBS III-RTTc | 273 | 360 | 0.8 | 24 | 72 |
| GBS III-TT | 264 | 460 | 0.6 | 14 | 46 |
| GBS V-RTTc | 341 | 370 | 0.9 | 26 | 84 |
| GBS V-TT | 218 | 305 | 0.7 | 19 | 70 |

Another method of coupling the above polysaccharides to tetanus C fragment, besides reductive amination is described in W00010599A2 patent application. The method involves first re-N-acryloylation of partially or totally de-Nacetylated polysaccharide followed by direct coupling of the activated polysaccharide to the carrier protein at pH 9-10. The chemistry is a Michael addition of the primary amino groups on the protein (u-NH2 of lysinyl residues) to the unsaturated N-acryloyl groups on the polysaccharide.

Example 2

Peclinical Evaluation of rTTc Conjugates

Potency of meningococcal conjugates—Schedule of immunization: 4-6 weeks old Swiss Webster female mice were immunized s.c. at days 0, 28 and 42 with 2 µg of polysaccharide conjugated to either TT (tetanus toxoid) or rTTc. Animals were bled at days 0, 28 and 52. Polysaccharide-specific IgG were measured by ELISA using respective C, Y or W polysaccharides human serum albumin conjugates as the coating antigen and prepared in a similar fashion as for the tetanus conjugate vaccines. Tetanus toxin antibodies raised to the conjugates were measured by ELISA with tetanus toxoid as the coating antigen. Antibody-complement mediated killing of antisera were determined by a Serum bactericidal assay (SBA) using baby rabbit serum as the source of complement.

Figure 4:
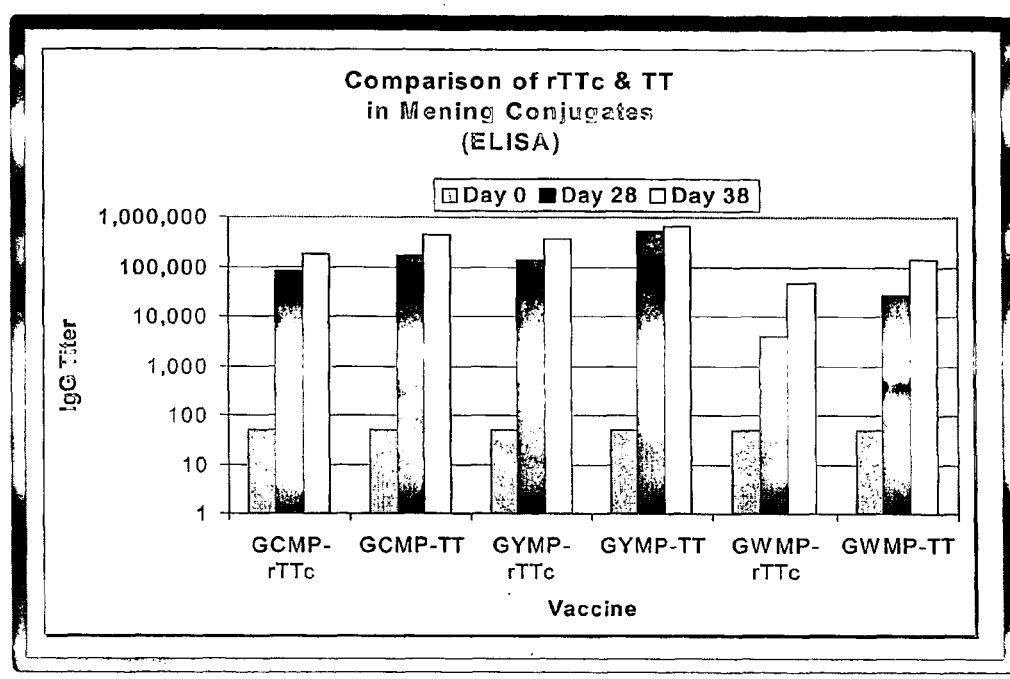
FIG. 4 depicts comparisons of recombinant Fragment C and the Tetanus Toxoid with meningococcal conjugates.
Figure 4:
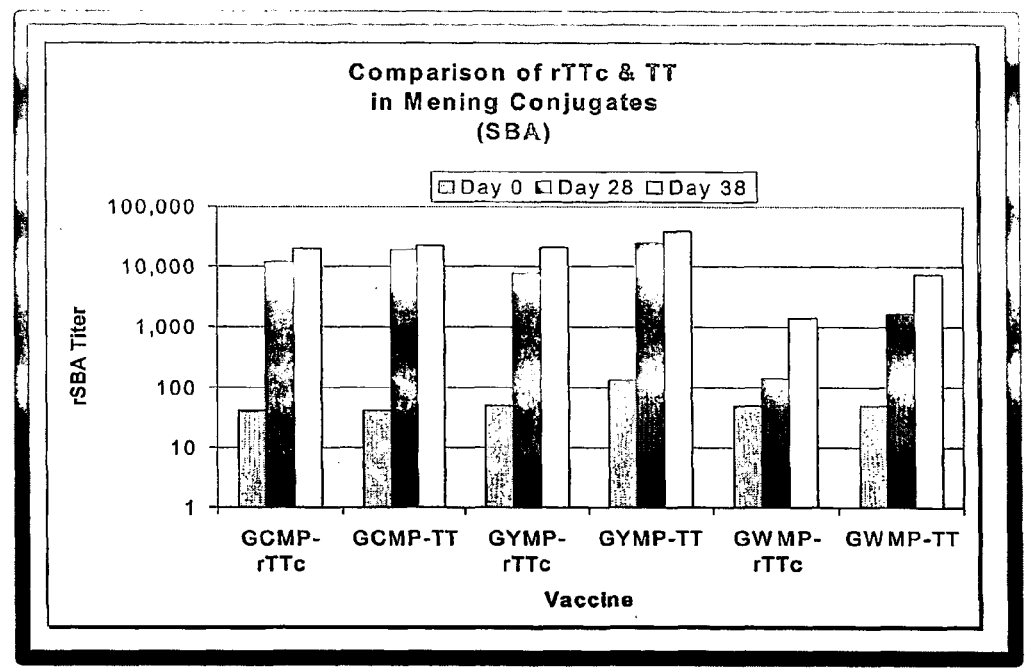

The potency (polysaccharide-specific IgG and serum bactericidal activity) to these conjugates is shown in FIG. 3 for a comparison between TTc, rTTc and TT conjugates of GCMP and in FIG. 4 for the corresponding immune response to conjugates of GYMP, GWMP and GCMP bound to either TT or rTTc.

As shown in FIG. 3 and FIG. 4, meningococcal rTTc conjugates do not display significant differences in potency when compared to their corresponding TT constructs. In addition, the anti-tetanus response and anti-tetanus C fragment (TTc) was also measured by a series of ELISAs. Significant anti-tetanus response in antisera to GCMP-TT conjugates was basically abolished in sera raised with TTc and rTTc GCMP conjugates as shown in Table 3.

Three assays were used: (a) Double antigen ELISA for Tetanus, (b) Indirect Tetanus IgG ELISA, (Rristiansen et al., APMIS 105:843-53 (1997), (c) Indirect Recombinant Tetanus toxin fragment C IgG ELISA. The assays were incubated at 4 to 8° C. over night. Assay a and b plates were coated with Tetanus toxoid lot 57 SSI diluted 1:10000 in carbonate buffer pH 9.6, and incubated at 4 to 8° C. over night. Plate(s) for assay c was done with reconstituted Recombinant Tetanus toxin Fragment C (rTTc)—lot 85161832, Roche—in 0.1M $NaHCO_3$ diluted to 1 µg/ml in carbonate buffer pH 9.6, and incubated for 2 hours at room temperature. One plate of each coating was applied the same pre-dilutions of samples and standards. Incubation was conducted over night at 4-8° C.

For detection, the Biotin-TT/HRP-Streptavidin system was used for assay a) and HRP-Goat anti Mouse IgG (Fc) 1:5000 was used for assays b) and c). The chromogene O-Phenylene Diamine (OPD) at a concentration of 1 mg/mL was used as substrate and the reaction was stopped with 2M $H_2SO_4$. The OD (optical density) was read at 492 nm. Data was analyzed using a reference line method.

The anti-rTTc MAb was used to standardize the IgG ELISA data, based on the data from the Double Antigen ELISA. The MAb to rTTc recognizes soluble toxoid as well as coated native Tetanus toxoid and the Fragment C to the same extent. It also indicates that antibodies raised to rTTc can be measured by the three types of ELISAs.

The data presented in Table 3 indicate that a very significant anti-tetanus IgG response was measured in antisera to GCMP-TT conjugates, but this response was practically absent in sera raised against TTc and rTTc GCMP conjugates.

Figure 5:
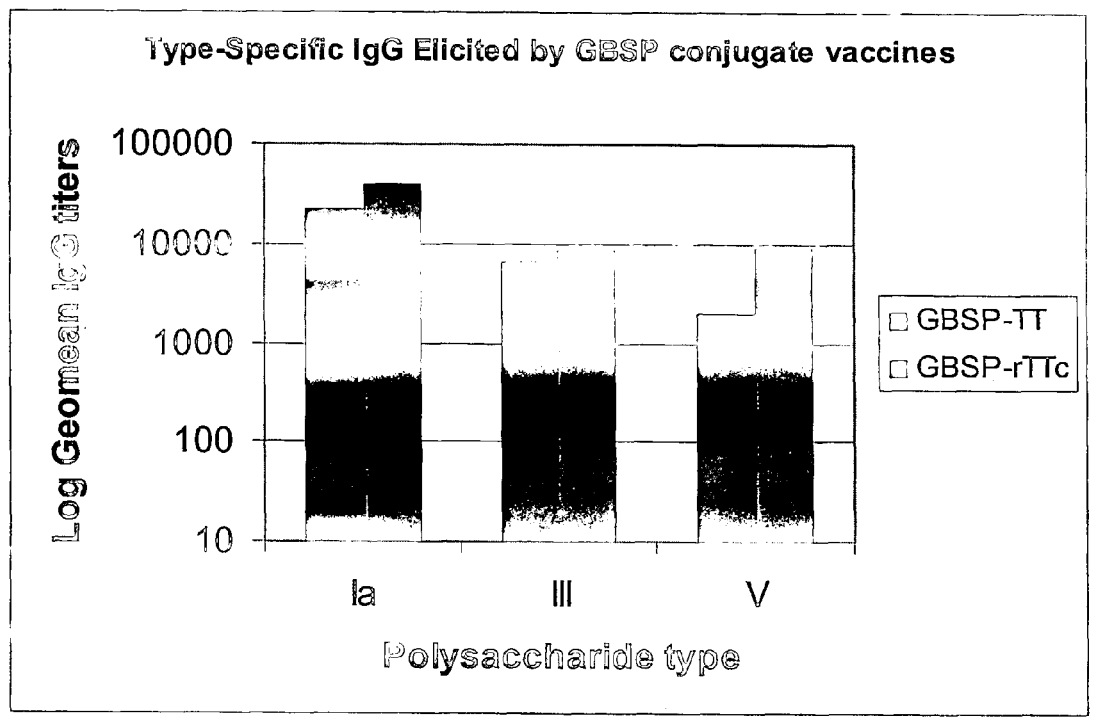
FIG. 5 depicts type-specific IgG elicited by Group B *Streptococcus* polysaccharide (GBSP) conjugates with Tetanus Toxoid or recombinant Fragment C.

GBS conjugates using either TT or rTTc as the carrier protein were tested for their ability to elicit a protective immune response. The efficacy of the monovalent types Ia, III and V conjugates prepared as described herein was evaluated in the neonatal mice model of Madoff et al. Infec. & Immun. 60:4989-94 (1992). Animals (CD1 female mice) were inoculated or the combination tetravalent vaccine mix, Each animal received 1 p.g of each of the conjugated type-polysaceharide at days 0 and 21. Vaccines were adsorbed on Aluminum hydroxide (Superfos, Denmark). Mice were impregnated at day 21. Neonates were challenged 48 hours following birth with either GBS type Ia (090), GBS type III (M781), or GBS type V (CJ111). The GBS type-specific polysaccharide IgG induced by each individual conjugate are shown in FIG. 5. The data indicate that type Ia- and III-rTTc conjugates elicit similar if not better polysaccharide-specific IgG titers than their corresponding TT counterpart, however type V-rTTc conjugates elicit significantly higher type V specific IgG than their corresponding TT.

Efficacy results from the neonatal mice challenge correlate well with the antibody surrogate levels, that is, there is a significantly better protection against type V challenge afforded with the V-rTTc conjugates (ca 85% efficacy) than with V-TT (ca 65%), whereas similar protection was provided

Figure 6:
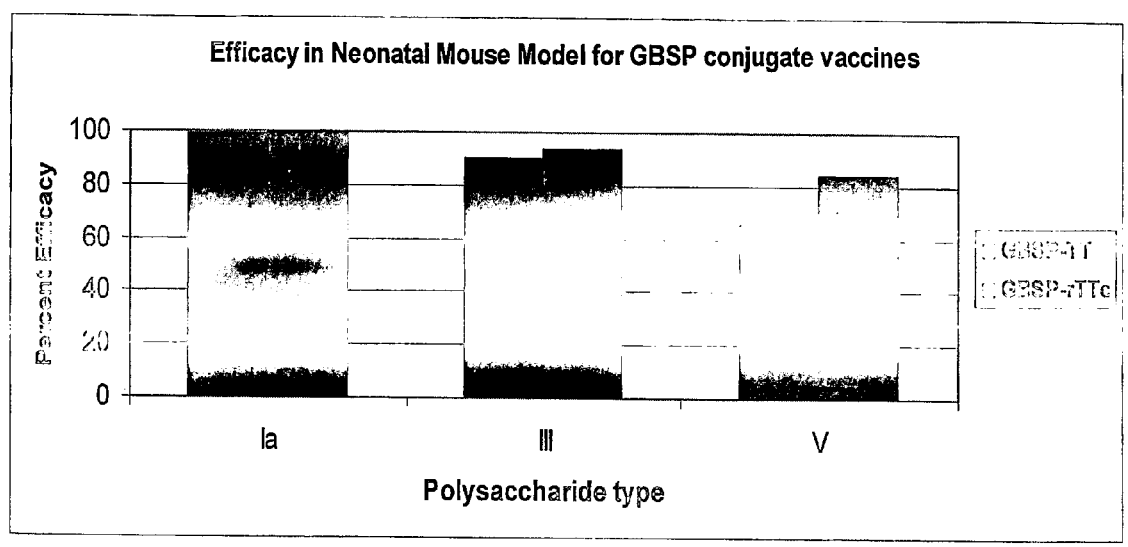
FIG. 6 depicts the efficacy of GBSP conjugates in a neonatal mouse model.

| | ELISA (IU/mL) | | | | | | | |
|---|---|---|---|---|---|---|---|---|
| | Double Antigen | | | | Indirect TT | | Indirect rTTc | |
| | Day 0 | Day 28 | Day 38 | Day 52 | Day 38 | Day 52 | Day 38 | Day 52 |
| GCMP-TT | <0.002 | 4.98 | 72.1 | 54.5 | 170.3 | 102.6 | 7.2 | 10.4 |
| GCMP-rTTc | <0.002 | <0.02 | <0.002 | 0.006 | 0.12 | 0.20 | 13.6 | 19.7 |
| GCMP-TTc | <0.002 | <0.02 | <0.002 | 0.003 | 0.001 | 0.05 | 0.55 | 2.3 |
| Anti rTTc Mab | | 24.0 | | | 20.1 | | 20.1 | | against challenge with type Ia and III GBS organisms with close to 100% efficacy against Ia, 90-95% against III with either one of the corresponding rTTc or TT conjugates. See FIG. 6. It should be noted that in the murine model, type V challenge is the most difficult to overcome following immunization with the polysaccharide conjugate, and thus it is significant that tetanus fragment C as a carrier protein for type V polysaccharide is a demonstrably better carrier protein than the whole tetanus molecule.

The anti-tetanus response generated with the GBS TT and rTTc conjugates as well as the residual TT activity measured in Lf units (measuring flocculation) are shown in Table 4.

TABLE 4

| Vaccine | Mean IU/mi | % >= 0.01 IU/mI | Mean LF/ml | % of expected |
|---|---|---|---|---|
| PBS | Nd | nd | <0.007 | NA |
| $GBSP_{Ia}$-TT | 40.0 | 100 | 0.261 | 6.5 |
| $GBSP_{Ia}$rTTc | 0.0034 | 10 | <0.007 | NA |
| $GBSP_{III}$-TT | 19.0 | 100 | 0.094 | 2.4 |
| $GBSP_{III}$rTTc | <0.002 | 0 | <0.007 | NA |
| $GBSP_{v}$-TT | 27.8 | 100 | 0.059 | 1.5 |
| $GBSP_{v}$-rTTc | 0.0124 | 30 | <0.007 | NA |

This study is based on the assumption that the protein concentration is 10 μg/mL, the expected concentration is set to 4 Lf/mL for TT and 10 Lf/mL for rTTc.

Data from Table 4 indicate that the anti-tetanus IgG response in the sera induced by the rTTc conjugates is dramatically reduced when compared to the response induced by the corresponding TT conjugates. In addition, the number of tetanus toxin B-cell epitopes retained after conjugation of the C fragment to the GBS polysaccharides is virtually reduced to zero when compared to the same B-cell epitopes retained in the corresponding TT conjugates. Accordingly, the data presented in Table 3 and Table 4 support and demonstrate further advantages of the present invention in overcoming potential carrier-induced epitopic suppression of the antibody response to polysaccharide conjugate vaccine containing tetanus as the carrier protein.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

What is claimed is:

1. A conjugated vaccine comprising bacterial capsular polysaccharide antigen that has been conjugated to Fragment C, wherein the Fragment C does not exist in the conjugate vaccine as part of a whole tetanus toxoid molecule, and wherein the conjugate vaccine does not increase a patient's anti-tetanus titer response.

2. The conjugated vaccine according to claim 1, wherein the bacterium is selected from the group consisting of *Meningococcus* group A, B, C, Y, W135 and X; *Streptococcus* group A, B, and C; *Pneumococcus* types 1, 2, 3, 4, 6A, 6B, 9, 14, 18F, 19F and 23; *Staphylococcus aureus* types 5 and 8 and *Haemophilus influenzae* type b.

3. The conjugate vaccine according to claim 1, wherein the Fragment C is obtained by recombinant expression.

4. The conjugate vaccine according to claim 1, wherein the Fragment C is obtained from a tetanus toxoid molecule via digestion of the tetanus toxoid molecule by a protease.

5. The conjugate vaccine according to claim 4, wherein the protease is papain.

6. The conjugate vaccine according to claim 2, wherein the bacterium is selected from the group consisting of *Streptococcus* group A, B, and C.

* * * * *